US012564366B2

(12) United States Patent
Fang et al.

(10) Patent No.: US 12,564,366 B2
(45) Date of Patent: Mar. 3, 2026

(54) SYSTEMS AND METHODS FOR IMAGE DENOISING VIA ADVERSARIAL LEARNING

(71) Applicant: University of Florida Research Foundation, Inc., Gainesville, FL (US)

(72) Inventors: Ruogu Fang, Gainesville, FL (US); Peng Liu, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 261 days.

(21) Appl. No.: 18/007,366

(22) PCT Filed: Jul. 29, 2021

(86) PCT No.: PCT/US2021/043635
§ 371 (c)(1),
(2) Date: Jan. 30, 2023

(87) PCT Pub. No.: WO2022/026661
PCT Pub. Date: Feb. 3, 2022

(65) Prior Publication Data
US 2023/0301614 A1     Sep. 28, 2023

Related U.S. Application Data

(60) Provisional application No. 63/058,008, filed on Jul. 29, 2020.

(51) Int. Cl.
A61B 6/00          (2024.01)
A61B 6/58          (2024.01)
(Continued)

(52) U.S. Cl.
CPC .......... *A61B 6/5258* (2013.01); *A61B 6/5235* (2013.01); *A61B 6/583* (2013.01);
(Continued)

(58) Field of Classification Search
CPC ................................................. A61B 6/5258
See application file for complete search history.

(56) References Cited

U.S. PATENT DOCUMENTS

2018/0018757 A1     1/2018   Suzuki
2020/0065940 A1     2/2020   Tang et al.

OTHER PUBLICATIONS

International Search Report for PCT/US21/43635 mailed Nov. 1, 2021.
(Continued)

*Primary Examiner* — Joseph M Santos Rodriguez
(74) *Attorney, Agent, or Firm* — Thomas | Horstemeyer, LLP

(57) ABSTRACT

Various examples are provided related to reconstructing images such as, e.g., medical images from low-dose image scans. Adversarial learning such as, e.g., a Cyclic Simulation and Denoising (CSD) framework can be used to address challenges of complicated mixed noise in real low-dose scans. The CSD framework can include a simulator model that can extract low-dose noise and features (e.g., tissue features) from separate image spaces into a unified feature space and a denoiser model that can learn how to remove noise and restore features, simultaneously. Both the simulator model and the denoiser model can regularize each other in a cyclic manner to optimize network learning effectively. The CSD framework in combination with phantom scans can embrace the realistic low-dose noise and features into a unified learning environment to address the challenge of real low-dose image restoration.

11 Claims, 5 Drawing Sheets

(51) Int. Cl.
    G06T 5/50         (2006.01)
    G06T 5/70         (2024.01)

(52) U.S. Cl.
    CPC .................. G06T 5/50 (2013.01); G06T 5/70
        (2024.01); *G06T 2207/20081* (2013.01); *G06T*
        *2207/30004* (2013.01); *G06T 2207/30168*
        (2013.01)

(56) References Cited

OTHER PUBLICATIONS

Ronneberger, et al., "U-Net: Convolutional Networks for Biomedical Image Segmentation", Springer International Publishing Switzerland MICCAI, Nov. 2015.

Yuan, et al., "Low-dose CT image denoising without high-does reference images", Proceedings of SPIE; 15th International Meeting on Fully Three-Dimensional Image Reconstruction in Radiology and Nuclear Medicine, May 28, 2019.

Goldman, et al., "Reducing Radiation Dose in Body CT: A Practical Approach to Optimizing CT Protocols", Medical Physics and Informatics, Review; Aug. 3, 2012.

Shaker, et al., "Fully Convolutional Architecture for Low-Dose CT Image Noise Reduction" IOP Conference Series Materials Science and Engineering, Aug. 2017.

Zhang, et al., "Beyond a Gaussian Denoiser: Residual Learning of Deep CNN for Image Denoising", IEEE Transactions On Image Processing, vol. 26, No. 7, Jul. 2017.

Britten, et al., "The addition of computer simulated noise to investigate radiation dose and image quality in images with spatial correlation of statistical noise: an example application to X-ray CT of the brain", The British Journal of Radiology, 77, Apr. 2004.

Yang, et al. "Low-Dose CT Image Denoising Using a Generative Adversarial Network With Wasserstein Distance and Perceptual Loss", IEEE Transactions On Medical Imaging, vol. 37, No. 6, Jun. 2018.

Wang, et al., "Low-dose preview for patient-specific, task-specific technique selection in cone-beam CT", Med. Phys. 41 (7) Jul. 2014.

Power, et al., "Computed tomography and patient risk: Facts, perceptions and uncertainties", World of Journal of Radiology, Dec. 2016.

Zhu, et al., "Unpaired Image-to-Image Translation using Cycle-Consistent Adversarial Networks", ICCV, Mar. 30, 2017.

FIG. 4

Table 2

| mAs | PSNR (dB) / SSIM | |
|-----|------------------|--|
| | End-to-end | CSD(ours) |
| 30 | 31.93/0.9105 | 32.05/0.9124 |
| 60 | 33.33/0.9365 | 33.92/0.9429 |

FIG. 5

SYSTEMS AND METHODS FOR IMAGE DENOISING VIA ADVERSARIAL LEARNING

CROSS REFERENCE TO RELATED APPLICATIONS

This application is the 35 U.S.C. § 371 national stage application of PCT Application No. PCT/US2021/043635, filed Jul. 29, 2021, which claims priority to, and the benefit of, U.S. provisional application entitled "Systems and Method for Reconstructing Realistic Noisy Medical Images having Ser. No. 63/058,008, filed Jul. 29, 2020, both of which are hereby incorporated by reference herein in their entireties.

STATEMENT OF GOVERNMENT INTEREST

This invention was made with government support under Grant No. 1908299, awarded by the National Science Foundation. The government has certain rights in this invention.

TECHNICAL FIELD

The invention relates to systems and methods for performing high-quality image reconstruction of images such as, e.g., medical images that contain noise due to image acquisition conditions such as, for example, imaging with low doses of radiation, using shorter scanning times during image acquisition and using lower tracer dose.

BACKGROUND

Noisy images are prevalent in our daily life and technology. For example, medical imaging (e.g., computed tomography (CT), magnetic resonance imaging (MRI), positron emission tomography (PET), etc.) plays a vital role in diagnosing and guiding the treatment of injuries and diseases. The radiation exposure to patients in medical imaging, however, has led to tremendous concerns about causing cancers or other negative health conditions.

Reducing radiation dose is a low-cost approach to addressing these concerns. Nevertheless, methods that rely on dose reduction introduce noise into the image scans, hindering the diagnostic effectiveness of such scans. Several studies have been proposed to address this problem by removing the noise from such low-dose scanned images. All of these proposed approaches either involve an image prior or learning a mapping function between high and low-dose scans based on Gaussian noise simulation. However, the real low-dose noise is a mixed distribution that is difficult to simulate and to remove, thus preventing such methods from being practiced.

The development of deep learning (DL) algorithms has led to significant advances in image denoising. Most of the success relies on supervised learning on a large number of labeled images, and some recent work has proposed modeling the denoiser only from noisy images based on several assumptions (e.g., noise statistical independence). However, there are significant challenges for these approaches. First, real low-dose scans are generally not available. Second, the real low-dose noise shows some correlation across different properties (e.g., distribution and intensity). Thus, these assumptions are not always guaranteed in practical scenarios.

A need exists for a novel approach to noisy images that overcomes these challenges to achieve robust image reconstruction and healthcare risk reduction.

SUMMARY

An adversarial machine learning system is disclosed comprising a memory device and a processor configured to perform a simulator model and a denoiser model. For example, cyclic simulation and denoising (CSD) is one type of adversarial learning system. During a simulation-to-denoising (S2D) training cycle, the simulator model receives as input a low-dose noisy phantom image scan and a high-dose patient image scan and uses the low-dose noisy phantom image scan and the high-dose patient image scan to generate a simulated low-dose noisy patient image scan. The denoiser model receives the simulated low-dose noisy patient image scan output from the simulator model and uses the low-dose noisy patient image scan to train the denoiser model to remove noise from a real low-dose noisy patient image scan. Phantom image scans can be obtained with an anthropomorphic physical phantom model.

In accordance with various aspects, the denoiser model can operate as a regularizer for the simulator model during the S2D learning cycle by outputting feedback to the simulator model characterizing a quality of the simulated low-dose noisy patient image scan output by the simulator model. The simulator model can use the feedback to train the simulator model to improve the quality of the simulated low-dose noisy patient image scan.

In accordance with one or more aspects, during a denoising-to-simulation (D2 S) training cycle, the denoiser model can receive as input a low-dose noisy patient image scan and a low-dose noisy phantom image scan and can use the low-dose noisy patient image scan and the low-dose noisy phantom image scan to generate a high-dose patient image scan. The simulator model can receive the high-dose patient image scan output from the denoiser model and can use the high-dose patient image scan and the low-dose noisy phantom image scan to train the simulator model to generate the simulated low-dose noisy patient image scan. The simulator model can operate as a regularizer for the denoiser model during the D2S learning cycle by outputting feedback to the denoiser model that the denoiser model can use to train the denoiser model to improve the quality of the high-dose patient image scan outputs by the denoiser model.

In accordance with another aspect, an adversarial learning and denoising method comprises: during a simulation-to-denoising (S2D) training cycle, receiving as input in a simulator model a low-dose noisy phantom image scan and a high-dose patient image scan and outputting a simulated low-dose noisy patient image scan; and during the S2D training cycle receiving the simulated low-dose noisy patient image scan output from the simulator model in a denoiser model and using the low-dose noisy patient image scan in the denoiser model to train the denoiser model to remove noise from a real low-dose noisy patient image scan. Phantom image scans can be obtained with an anthropomorphic physical phantom model.

In accordance with various aspects, the adversarial learning and denoising method can further comprise: during the S2D training cycle, operating the denoiser model as a regularizer for the simulator model by outputting feedback to the simulator model characterizing a quality of the simulated low-dose noisy patient image scan output by the simulator model; and during the S2D training cycle, using the feedback in the simulator model to train the simulator model to improve the quality of the simulated low-dose noisy patient image scan.

In accordance with one or more aspects, the adversarial learning and denoising method can further comprise: during a denoising-to-simulation (D2 S) training cycle, receiving as input in the denoiser model a low-dose noisy patient image scan and a low-dose noisy phantom image scan and using the low-dose noisy patient image scan and the low-dose noisy phantom image scan to remove noise from the low-dose noisy patient image scan to generate a high-dose patient image scan; and during the D2S training cycle, receiving the high-dose patient image scan output from the denoiser model in the simulator model and using the high-dose patient image scan to train the simulator model to generate the low-dose noisy patient image scan. During the D2 S training cycle, the simulator model can operate as a regularizer for the denoiser model by outputting feedback to the denoiser model. During the D2S training cycle, the feedback output by the simulator model can be used in the denoiser model to train the denoiser model to improve the quality of the high-dose patient image scan generated by the denoiser model.

In accordance with another aspect, a medical imaging system for reconstructing medical images from noisy medical image scans comprises an image acquisition system that acquires a real low-dose noisy patient image scan, a memory device, and a processor configured to execute a trained denoiser model that has been trained in accordance with a cyclic simulation and denoising (CSD) machine learning method comprising a simulation-to-denoising (S2D) training cycle during which a simulator model receives as input a low-dose noisy phantom image scan and a high-dose patient image scan and uses the low-dose noisy phantom image scan and the high-dose patient image scan to generate a simulated low-dose noisy patient image scan that the denoiser model receives and uses to train the denoiser model to remove noise from the real low-dose noisy patient image scan. Phantom image scans can be obtained with an anthropomorphic physical phantom model.

In accordance with various aspects, the CSD machine learning method can further comprise a denoising-to-simulation (D2S) training cycle during which the denoiser model receives as input a low-dose noisy patient image scan and a low-dose noisy phantom image scan and uses the low-dose noisy patient image scan and the low-dose noisy phantom image scan to generate a high-dose patient image scan. The simulator model receives the high-dose patient image scan output from the denoiser model and uses the high-dose patient image scan and the low-dose noisy phantom image scan to train the simulator model to generate the simulated low-dose noisy patient image scan.

In accordance with one or more aspects, the simulator model can operate as a regularizer for the denoiser model during the D2S learning cycle by outputting feedback to the denoiser model that the denoiser model can use to train the denoiser model to improve the quality of the high-dose patient image scan outputs by the denoiser model.

In accordance with some aspects, the denoiser model can operate as a regularizer for the simulator model during the S2D training cycle by outputting feedback to the simulator model characterizing a quality of the simulated low-dose noisy patient image scan output by the simulator model, and wherein during the S2D training cycle. The simulator model can use the feedback to train the simulator model to improve the quality of the simulated low-dose noisy patient image scan.

In accordance with another aspect, a method for reconstructing medical images from noisy medical image scans comprises: with an image acquisition system, acquiring a real low-dose noisy patient image scan; and in a processor, executing a trained denoiser model that removes noise from the real low-dose noisy patient image scan to reconstruct a medical image from the real low-dose noisy patient image scan. The trained denoiser model has been trained in accordance with a cyclic simulation and denoising (CSD) machine learning method comprising a simulation-to-denoising (S2D) training cycle during which a simulator model receives as input a low-dose noisy phantom image scan and a high-dose patient image scan and uses the low-dose noisy phantom image scan and the high-dose patient image scan to generate a simulated low-dose noisy patient image scan that the denoiser model can receive and use to train the denoiser model to remove noise from low-dose noisy patient image scans. Phantom image scans can be obtained with an anthropomorphic physical phantom model.

In accordance with various aspects, the CSD machine learning method can further comprise a denoising-to-simulation (D2S) training cycle during which the denoiser model receives as input a low-dose noisy patient image scan and a low-dose noisy phantom image scan and uses the low-dose noisy patient image scan and the low-dose noisy phantom image scan to train the denoiser model to generate a high-dose patient image scan from a real low-dose patient image scan. The simulator model can receive the high-dose patient image scan from the denoiser model during the D2S training cycle and can use the high-dose patient image scan and the low-dose noisy phantom image scan to train the simulator model to generate the simulated low-dose noisy patient image scan.

In accordance with one or more aspects, the simulator model can operate as a regularizer for the denoiser model during the D2S learning cycle by outputting feedback to the denoiser model that the denoiser model can use to train the denoiser model to improve the quality of the high-dose patient image scan outputs by the denoiser model.

In accordance with some aspects, during the S2D training cycle, the denoiser model can operate as a regularizer for the simulator model by outputting feedback to the simulator model characterizing a quality of the simulated low-dose noisy patient image scan output by the simulator model. During the S2D training cycle, the simulator model can use the feedback to train the simulator model to improve the quality of the simulated low-dose noisy patient image scan generated by the simulator model.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

FIG. 4 shows a table with an example of the average PSNR(dB)/SSIM of noise removal performance for a deep neural network trained through the CSD framework of the present disclosure and the standard end-to-end way.

FIG. 5 shows an example of a visual comparison of the denoising performance between the network trained in an end-to-end manner and the one trained with the CSD framework of the present disclosure.

DETAILED DESCRIPTION

In accordance with representative embodiments, a data-driven, deep learning (DL)-based framework is disclosed for imaging such as, e.g., low-dose medical imaging. The framework is referred to herein as an adversarial framework such as, e.g., a Cyclic Simulation and Denoising (CSD) framework. The CSD framework addresses the aforementioned challenge of complicated mixed noise in real low-dose scans. In addition, an anthropomorphic physical phantom model can be incorporated into generative adversarial networks. The physical model can provide paired low-dose and high-dose phantom scans (e.g., CT scans) before scanning the actual patients. These phantom scans can offer statistical noise, which is related to the specific CT machine, to precisely capture noise properties and remove real complex noise from CT scans. A simulation model is built that can take a noise-free high-dose scan as input to generate its noisy low-dose version. Noise simulation facilitates the denoising module in understanding the realistic noise property. Realistic low-dose noise can be obtained by scanning on a physical phantom model for simulation. However, phantom scanning lacks tissue features. The missing tissue features prevent feasible phantom-based solutions for low-dose image restoration. In other words, a model trained with paired low-dose and high-dose phantom scans will fail to effectively remove real noise from low-dose patient scans. The CSD can train using normal-dose and phantom CT scans simultaneously to embrace realistic noise and tissue features into a unified learning framework without the access labeled or Gaussian noise simulated data.

Figures 1, 2A:
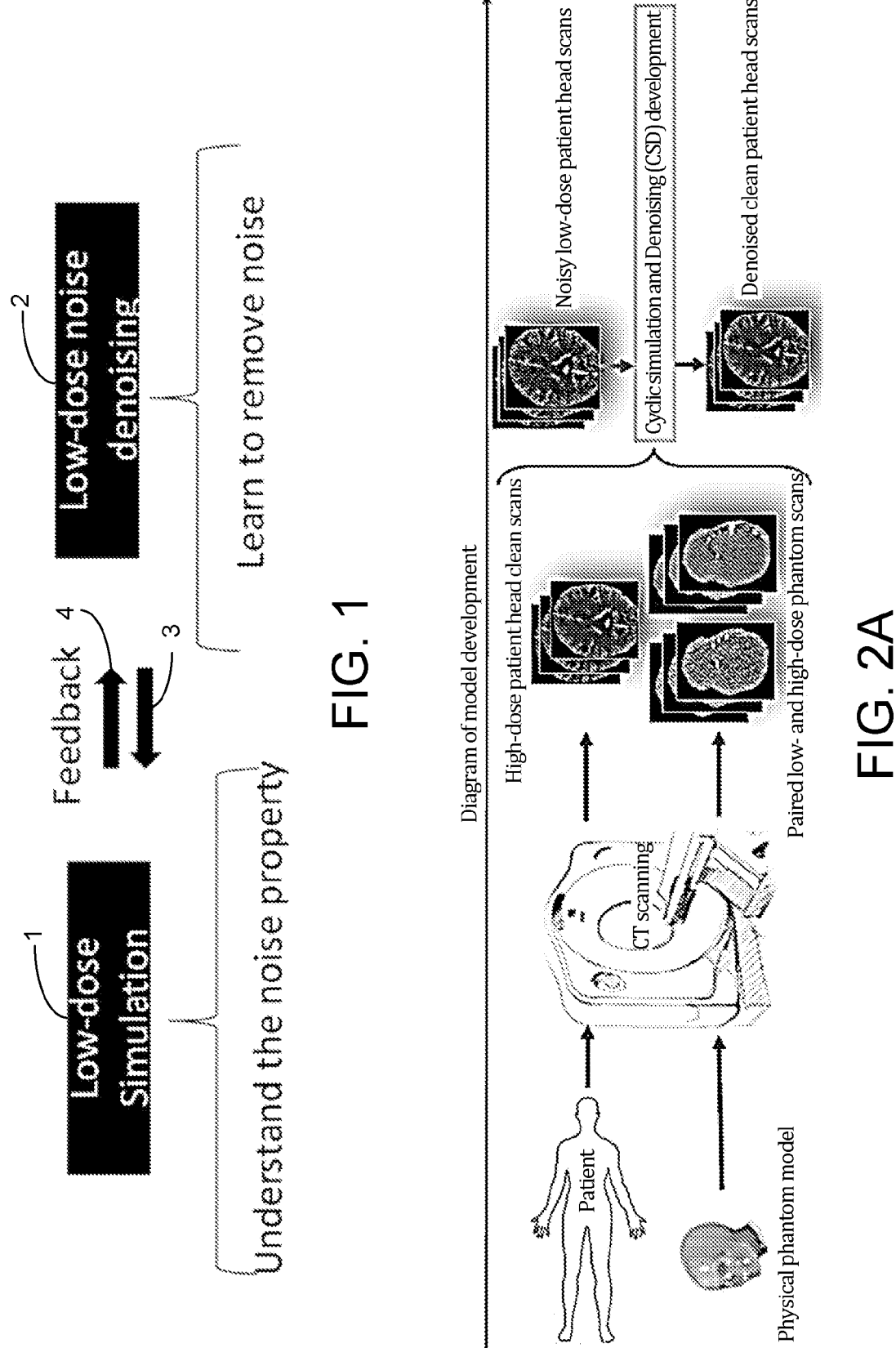
FIG. 1 shows a block diagram of an example of the CSD framework in accordance with a representative embodiment comprising a simulator and a denoiser and demonstrates the manner in which they interact.
FIG. 2A provides an example of an overview of the model development and incorporation of a physical phantom model into the CSD methodology in accordance with an embodiment FIGS. 2B-2D provide an example of an overview of the CSD methodology in accordance with an embodiment.

In accordance with a representative embodiment, the CSD framework overcomes this challenge by creating a dynamic interactive learning environment for a simulator and a denoiser. FIG. 1 shows a block diagram of the CSD framework in accordance with a representative embodiment comprising a simulator 1 and a denoiser 2 and demonstrates the manner in which they interact. The simulator 1 preferably is only used during training and is not used in a clinical setting, while the denoiser 2, once trained, is used in a clinical setting. The simulator 1 extracts low-dose noise and tissue features from two separate image spaces, namely, a low-dose noisy phantom and high-dose noise-free patient scans, into a unified feature space. This unified feature space facilitates the denoiser 2 in learning how to remove noise and restore tissue features, simultaneously. Meanwhile, the denoiser 2 provides feedback 3 to the simulator 1 on the quality of the generated noise. Both the simulator 1 and the denoiser 2 regularize each other in a cyclic manner to optimize network learning effectively. In the cycle from simulation to denoising, the simulator 1 performs simulation while using the denoiser 2 as its regularizer (feedback arrow 3). In the backward cycle from denoising to simulation (feedback arrow 4), the denoiser 2 performs denoising while using the simulator 1 as its regularizer. Thus, the CSD framework in combination with phantom CT scans embraces the realistic low-dose noise and tissue features into a unified learning environment to address the challenge of real low-dose CT image restoration.

In the following discussion, the CSD framework is thoroughly evaluated for its ability to remove both real low-dose and Gaussian simulated noise. The results show that the denoiser 2 built through the CSD framework outperforms state-of-the-art denoising algorithms and demonstrates significant clinical potential for low-quality image restoration. In the following disclosure, a data-driven framework is disclosed for image restoration via cyclic interaction between noise simulation and denoising in which phantom and deep learning are combined for real low-dose noise simulation and denoising. Incorporation of an anthropomorphic physical phantom model into generative adversarial learning to address the challenges of removing real noise from ultra-low-dose CT scans for radiation reduction and development of a unsupervised framework in the combination of phantom CT scans can outperform start-of-the-art methods without using any labeled or other noise simulation data.

It should be noted that while the examples, experiments and simulations disclosed herein are directed to low-dose CT imaging, the disclosed principles and concepts apply equally to other types of medical imaging technologies, such as, for example, MRI imaging and PET imaging (e.g., MM arterial spins, PET, etc.). In addition, the disclosed principles and concepts apply equally to other image acquisitions conditions that introduce noise into the image scan, such as, for example, reduced scan times, lower tracer dose, etc. The disclosed methodology can be applied to a wide variety of images with noise, such as natural images captured in dim light, surveillance image captured due to environmental noise, and satellite image due to signal noise and device technical limit, in addition to medical images including CT scanned at low radiation dose, and MM scanned at faster acquisition time.

Methodology

The problem of image denoising such as, e.g., CT image denoising can be understood by the equation $L=H+N$, where H is the clean, high-dose CT image, L is the noisy, low-dose CT image, and N is additive image noise. Though an additive relationship does not completely represent the relationship between clean and noisy images, this formula provides a baseline for understanding the problem.

We utilize two deep networks in the CSD framework. The first network $G_s$ is the noise simulator 1 and can be modeled by $L=G_s(H, \alpha)$, where $\alpha$ is the desired simulated dose level and implicitly indicated in training data. The second network $G_d$ is the denoiser 2 that can be modeled by $H=G_d(L)$, where $G_d$ is the network generating a noise-free image from a given low-dose noisy input L.

Unsupervised Learning by Incorporating Physical Model

A head phantom model can be used to obtain paired low-dose and high-dose phantom CT scans, with which the normal dose (high-dose) patient CT scans are combined to develop a CSD model. The phantom scans allow the model to access real noise properties and the patient scans offer the actual brain tissue features to the model. In this way, the need for noisy low-dose CT scans from actual patients and even the Gaussian noise simulated low-dose CT scans can be eliminated to develop the model. FIG. 2A illustrates an example of the model development and its incorporation. Therefore, we present an unsupervised learning framework by incorporating an anthropomorphic physical phantom model.

Cyclic Simulation and Denoising (CSD) Framework

Figures 2B, 2C, 2D:
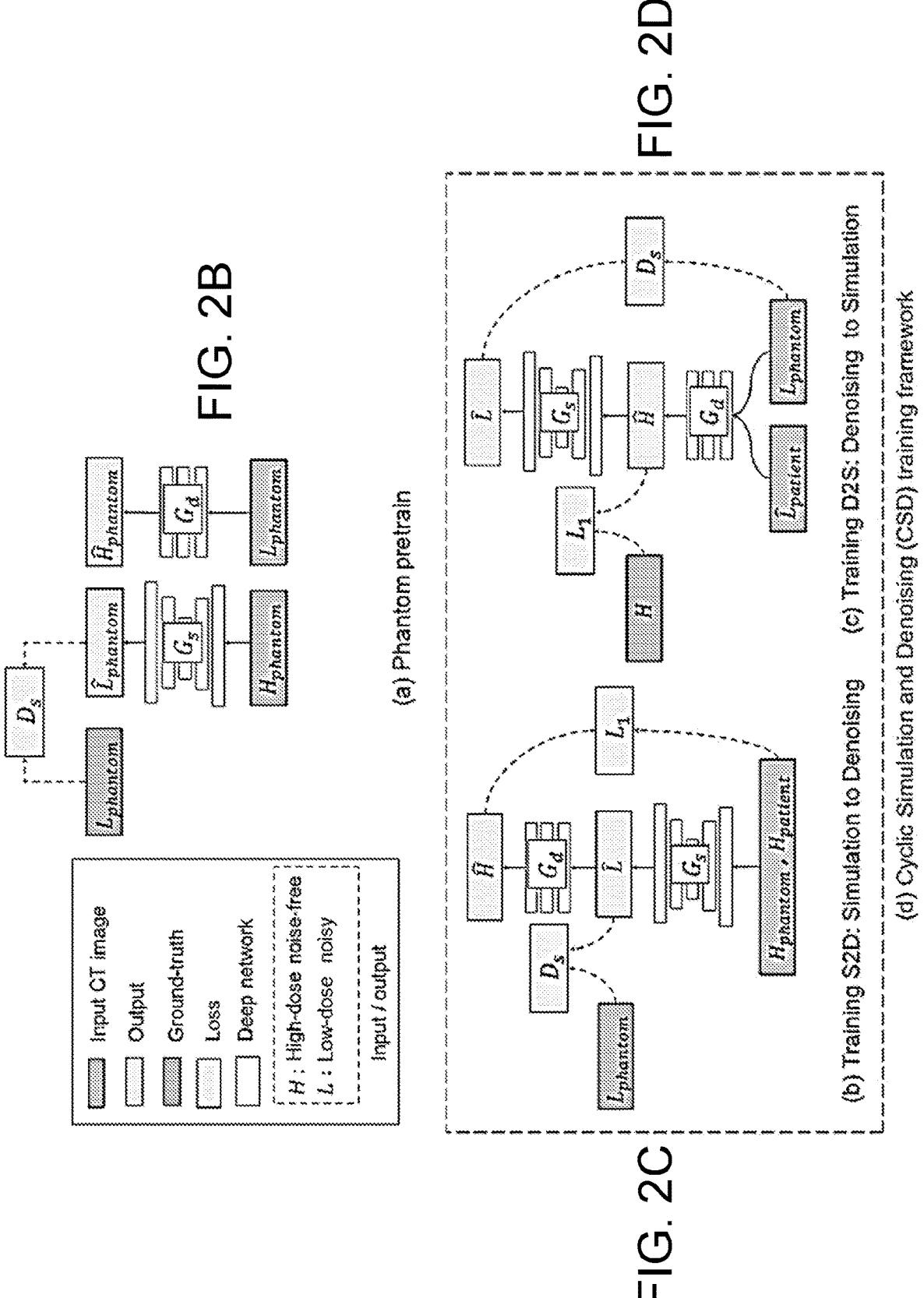
FIG. 2B represents using low- and high-dose phantom CT scans to generate the denoiser and simulator pre-trained models, respectively.
FIG. 2C represents the denoiser and simulator pre-trained models being used to perform S2D training.
FIG. 2D represents the denoiser and simulator pre-trained models being used to perform D2S training.

Overview: FIGS. 2B-2D provide an overview of the CSD methodology in accordance with an embodiment. We develop two deep networks to perform simulator and denoiser individually. To ease the network training, we first use paired low- and high-dose phantom CT scans to pre-train the simulator and denoiser, separately. FIG. 2B represents using low- and high-dose phantom CT scans to generate the denoiser and simulator pre-trained models, respectively. Then, we plug the simulator and denoiser pre-trained models into our CSD framework. FIGS. 2C and 2D represent the CSD framework. FIG. 2C represents the denoiser and simulator pre-trained models being used to perform simulation-to-denoising (S2D) training. FIG. 2D represents the denoiser and simulator pre-trained models being used to perform denoising-to-simulation (D2S) training.

In an embodiment, we start with noise simulation using both the phantom and patient CT scans to generate low-dose noisy patient CT images that simultaneously provide noise and tissue features for training the denoiser. Two training stages: first, we initialize the weights of the simulator and denoiser by pretraining on physical phantom CT scan, as shown in FIG. 2B. Then, the S2D cycle-training is performed, as shown in FIG. 2C, substantially simultaneously with the D2S cycle-training, as shown in FIG. 2D. $G_s$ and $G_d$ represent simulation and denoising, respectively. During training, the two cycles interact with each other and are executed, alternatively.

During the D2S cycle-training, the denoiser 1 takes phantom noisy scans and simulated noisy patient scans as input to learn how to remove realistic noise and restore tissue features simultaneously, while the simulator 2 mainly plays the role of a regularizer to the denoiser 2 for stabilizing the training. The interaction between simulator 1 and denoiser 2 forms the dynamic data-driven CSD framework to address the challenges of low-dose CT image restoration.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor", as that term is used herein encompasses an electronic component that can execute a computer program or executable computer instructions. References herein to a computer comprising "a processor" should be interpreted as a computer having one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating the disclosed principles and concepts.

Pretrain Simulator and Denoiser ($H \rightarrow \hat{L}$, $L \rightarrow \hat{H}$)

In this example, we train the simulator 1 with a u-shaped encoder-decoder generative adversarial network by formulating the objective as an adversarial learning. We use a discriminator $D_s$ to differentiate real low-dose CT images from fake samples generated by the simulator $G_s$. We illustrate the formulation of the simulation as follows.

$$\mathcal{L}_{GAN}(G_s, D_s) = \mathbb{E}_{L \sim p(L)}[\log(D_s(L))] + \mathbb{E}_{H_{phantom} \sim p(H)}[\log(1 - D_s(G_s(H_{phantom})))] \quad (1)$$

To encourage the outputs of the denoiser to match the noise-free phantom scans, we use an $\ell_1$ loss between the output and the ground truth image.

$$\mathcal{L}_1(G_d) = \mathbb{E}_{L,H \sim p(L,H)} \|H - G_d(L)\|_1 \quad (2)$$

Initializing the weights by pretraining (FIG. 2B) significantly eases the convergence of two interactive generators in both spatial and temporal space. However, the phantom scans still lack the essential features as scanning on a real patient.

Learn Simulation Interacting with Denoiser: S2D (H→L̂→Ĥ)

In this example, we start with noise simulation to provide both noise and tissue features for training the denoiser. We apply a discriminator $D_s$ to train the simulator $G_s$. We formulate the simulation objective as shown below.

$$\mathcal{L}_{GAN}^{S2D}(G_s, D_s) = \mathbb{E}_{L\sim p(L)}[\log(D_s(L))] + \mathbb{E}_{H\sim p(H)}[\log(1 - D_s(G_s(H)))] \quad (3)$$

In this example, the simulator feeds its output into the denoiser during training. Thus, we formulate the denoising loss using a modification of Equation 2 as follows.

$$\mathcal{L}_1^{S2D}(G_d) = \mathbb{E}_{L,H\sim p(L,H)}\|H - G_d(G_s(H))\|_1 \quad (4)$$

Besides the discriminator $D_s$, we take advantage of the denoising performance as regularization feedback to indicate the quality of the simulation. As the simulation becomes better, the denoising is getting harder. Furthermore, the discriminator $D_s$ in the S2D cycle takes the high-dose scans from both phantom and patients as inputs. The phantom data applies a latent constraint to the discriminator $D_s$ and stabilizes the training. Interacting with denoising encourages the simulator to generate realistic low-dose noise. Further, the denoiser benefits by taking the output of the simulator as additional training data, dynamically.

Learn Denoising in Simulator: D2S(L→Ĥ→L̂)

In this example, the development of the training process from denoising to simulation has two significant variations in terms of cycle consistency (see FIG. 2D). We first enable supervised learning to train the denoiser $G_d$ using the high-dose and the corresponding low-dose CT images. Compared to the adversarial learning, supervised learning provides a stronger supervision signal to build an accurate denoiser. More importantly, the simulator in the S2D cycle (FIG. 2C) produces the noise gradually close to the desired level during training. Thus, we can acquire various noise level images from the simulator, with which the denoiser self implicitly learns to restore noise-free CT scans for a range level of low-dose CT scans, rather than a specific noise level indicated in the training data. Therefore, the input to the denoiser $G_d$ in the D2S cycle (FIG. 2D) includes phantom low-dose and simulated patient low-dose images. We use $\ell_1$ loss to train the denoiser $G_d$. The $\ell_1$ loss encourages a pixel-wise match to the ground-truth. We illustrate the $\ell_1$ loss as given below.

$$\mathcal{L}_1^{D2S}(G_d) = \mathbb{E}_{L,H\sim p(L,H)}\|H - G_d(L)\|_1 \quad (5)$$

In this example, we instead use adversarial learning to train the simulator in D2S to address another challenge that is noise simulation aims to match the desired noise distribution rather than pixel-wise similarity. The objective to this adversarial learning the distribution is written as below.

$$\mathcal{L}_{GAN}^{D2S}(G_s, D_s) = \mathbb{E}_{L\sim p(L)}[\log(D_s(L))] + \mathbb{E}_{H\sim p(H)}[\log(1 - D_s(G_s(H)))] \quad (6)$$

For this example, we develop the cyclic simulation and denoising training with regularizations in both directions and take advantage of both cycles H→L̂→Ĥ and L→Ĥ→L̂. The total objective is illustrated as below.

$$G_s^*, G_d^* = \arg\min_{G_s,G_d}\max_{D_s}\lambda_1\mathcal{L}_{GAN}^{S2D}(G_s,D_s) + \quad (7)$$
$$\lambda_2\mathcal{L}_1^{S2D}(G_d) + \lambda_3\mathcal{L}_{GAN}^{D2S}(G_s,D_s) + \lambda_4\mathcal{L}_1^{D2S}(G_d)$$

where $\lambda$ indicates the weights of each loss. With these novel developments, the simulator and denoiser interact with each other in a cyclic self-learning manner to enable realistic noise simulation and accurate denoising for low-dose CT image.

EXPERIMENTS

Implementation Details
Network Architecture

For this example, for the simulator $G_s$, we adopt a standard u-shape architecture network (e.g., U-net) to map images from a denoised domain to a noisy domain. U-shape structure can combine the low-level with high-level features to generate realistic images. For the denoiser $G_d$, we use a stacked CNN (e.g., DnCNN) to restore noisy-free images by learning both noise and brain features from noisy inputs. A simple stacked convolutional network allows us to focus on the development of the insight of the proposed CSD framework. For discriminators $D_s$, we use a patch-based discriminator to classify (N×N) image patches as either simulated or real.

Datasets

For this example, we used three CT datasets during training and testing. The first dataset is obtained from the CT scanning on a single tissue-equivalent physical phantom model. This set contains various levels of low-dose series, scanned between 5 mAs and 95 mAs with 5 mAs intervals. In this experiment, we simply use 20 mAs, 30 mAs, and 60 mAs low-dose phantoms for training noise simulation and evaluating the reality of diverse types of noise. We also include the normal high-dose (175 mAs) scans as the noise-free ground-truth. Each dose level of phantom series produces 138 CT scans.

For this example, the second dataset used in the experiment is a public Retrospective Image Registration Evaluation (RIRE) dataset. This dataset includes 388 normal dose CT scans. We use 80% for training the simulator and denoiser in the proposed CSD and also task 20% for demonstrating the advantages of CSD over end-to-end training of a denoiser (Table 2 shown in FIG. 4), where we simulate the low-dose noise by adding Gaussian noise on normal dose CT scans. We compute the corresponding standard variation of Gaussian noise for a specific mAs.

Additionally, we acquire a real patient dataset including paired high-(190 mAs) and low-dose (20 mAs) in a total of 432 CT scans. We use them for comparing diverse types of simulated noise and evaluating real noise removal performance of our approach (Table 1 shown in FIG. 3), where 250 scans are used for training and 182 scans are used for testing. Moreover, we randomly select 373 scans from this dataset combining with 20% of the RIRE dataset, in total 449 scans included, to evaluate our CSD's advantages and generalizability (Table 2 shown in FIG. 4)

Image denoising performance was evaluated using peak signal-to-noise ratio (PSNR) and image structural similarity index measure (SSIM). In Table 1 (FIG. 3), the average PSNR(dB)/SSIM of real low-dose noise removal performance are given of a same deep neural network trained with Gaussian and CSD+phantom simulated low-dose noise, separately, in this example. The networks are trained on the simulated low-dose CT scans including noise levels mAs=30, 60. All models are tested on 182 real low-dose (20 mAs) CT scans. The best results are highlighted in bold. In Table 2 (FIG. 4), the average PSNR(dB)/SSIM of noise removal performance are given of the same deep neural network trained through the proposed CSD framework and the standard end-to-end way. The Gaussian simulated low-dose noise levels include mAs=30, 60. The best results are highlighted in bold.

We preprocess all three datasets by applying a brain mask to the selected center slices and extract the brain regions from each scan.

Training

In an embodiment, we apply learning rate 0.0001 and use 64×64 size of image patches as the input to train networks. We choose Adam as the optimizer and 128 as the batch size for all networks training. For loss weights λ, we experimentally apply 1, 1, 20, and 1 for $\mathcal{L}_{GAN}^{S2D}$, $\mathcal{L}_1^{S2D}$, $\mathcal{L}_1^{D2S}$, and $\mathcal{L}_{GAN}^{D2S}$, separately. We use these weights to balance the simulation and denoising. We weight the simulation more in the S2D cycle while applying more weights for denoising in D2S.

In an embodiment, we train our CSD with 3 iterations and 50 epochs each. In the first iteration, we only use the noisy phantom as the input of the $G_d$ in the D2S cycle for training. This strategy allows $G_d$ to intensively learn removing the complicated real noise from CT scans. In the following iterations, we combine the noisy patient scans generated by $G_s$ to continue the training of $G_d$ in the D2S cycle. This strategy enables $G_d$ to learn both noise and brain features, simultaneously, leading to a superior denoising performance. All experiments are processed on Python v3.6, and PyTorch v1.0.0 with Geforce GTX TITAN GPUs.

Results

Start with Simulation for Real Low-dose Noise Removal. In an embodiment, we aim to demonstrate that the proposed CSD framework in combination with a phantom can remove the real low-dose noise effectively. We first take the state-of-the-art medical image denoising network as a baseline and train it with Gaussian simulated low-dose CT scans at different noise levels. Then, we build the $G_d$ in CSD using the baseline's architecture and train it with paired low- and high-dose phantom CT scans at the same noise levels as Gaussian simulation.

In an embodiment, we test each model on 182 real low-dose CT scans at the noise level 20 mAs. The comparison results are shown at 20 mAs in Table and FIG. 3 at 30, 60 mAs noise levels. As one can see in FIG. 3, the combination of the proposed CSD training framework and phantom simulation significantly outperforms the baseline with an average 1.56 dB improvement on PSNR across three different noise levels.

Figure 3:
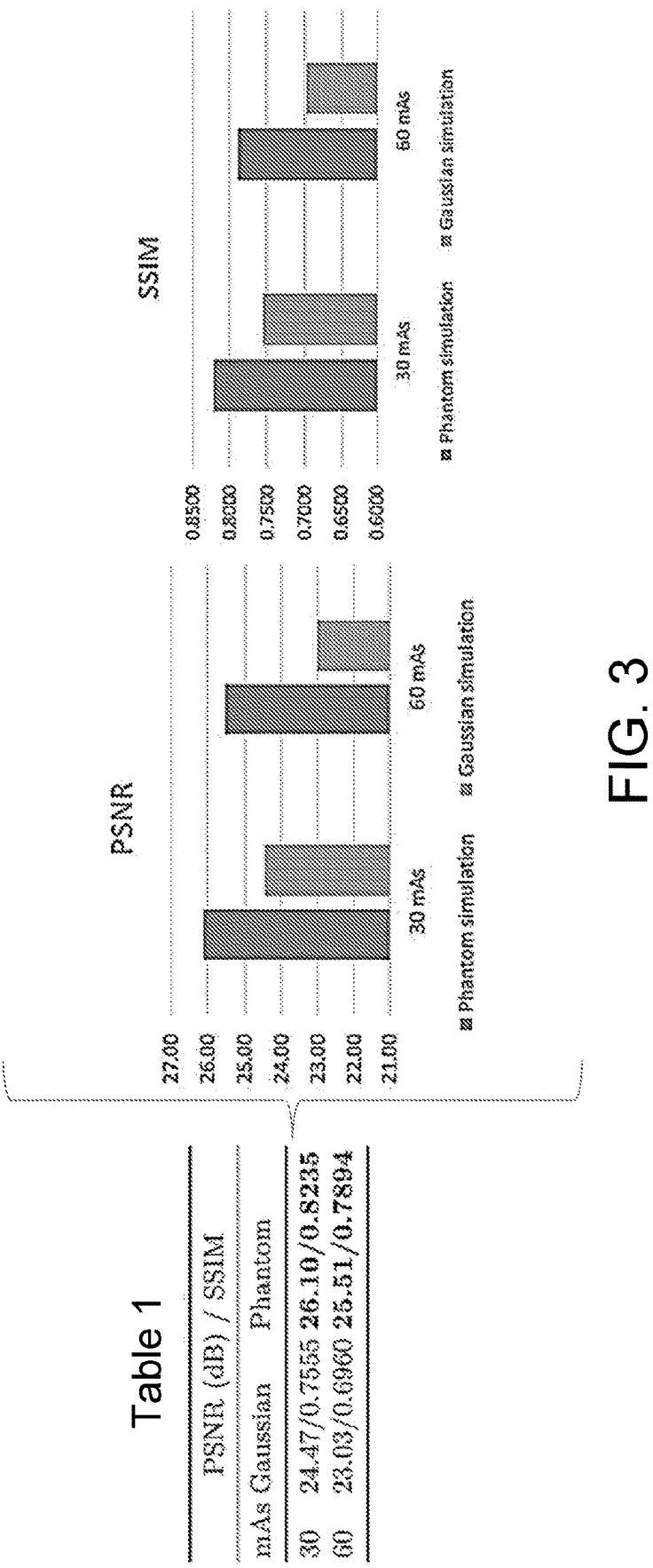
FIG. 3 shows a table with an example of the average PSNR(dB)/SSIM of real low-dose noise removal performance a deep neural network trained with Gaussian and CSD+phantom simulated low-dose noise, separately.

In an embodiment, as one can see in FIG. 3, the baseline network, which is trained with paired low- and high-dose phantom scans, performs much worse than the model trained with both our CSD phantom and Gaussian simulation, which may be due to the lack of critical tissue features in the phantom scans. Notably, these results indicate that CSD, in combination with phantom simulation, allows the denoiser to learn both real low-dose noise features from phantom and tissue image features from patient scans, simultaneously, leading to real low-dose noise removal with greater accuracy and precision.

Training State-of-the-art Denoiser with CSD. In this embodiment, we further evaluate the proposed CSD's generalizability to train a denoiser targeting the general simulated low-dose noise, such as Gaussian simulation. We still use the same baseline network to conduct this study. We use the standard end-to-end approach and our CSD framework to train two networks with the same architecture as the baseline, separately. Notably, to have a fair comparison, we only use original noisy CT scans in the training dataset as the input of the $G_d$ in D2S cyclic training. Then, we compare the two networks to remove 30 and 60 mAs levels of Gaussian simulated low-dose noise from 449 CT scans.

In this embodiment, as one can see in Table 2 below and in FIG. 4, the model trained with the CSD can consistently outperform the one trained in an end-to-end manner, with impressive average performance gain 0.355 dB for PSNR. In addition, we also show a visual result comparison in FIG. 5. FIG. 5 shows a visual comparison of the denoising performance between the network trained in an end-to-end manner and the one trained with our CSD framework.

In this embodiment, the denoiser $G_d$ trained with the CSD framework can produce more realistic CT scans from its low-dose noisy version. These results demonstrate that starting with simulation can create a live environment from which the denoiser can learn high-validity representations to achieve a better denoising performance. Theoretically, the simulator and denoiser in the CSD framework may play as a regularizer to each other to optimize the networks effectively.

As indicated above, while the disclosed principles and concepts have been described with reference to CT imaging for exemplary purposes, the disclosed principles and concepts apply to other types of medical imaging technologies where there is a need or desire to reconstruct high-quality medical images from noisy image scans, such as, for example, MRI imaging and PET imaging (e.g., MRI arterial spins, PET, etc.). In addition, the disclosed principles and concepts apply equally to other image acquisitions conditions that introduce noise into the image scan, such as, for example, reduced scan times, lower tracer dose, etc. For example, the methodology can be utilized for reconstructing a wide variety of images with noise, such as natural images captured in dim light, surveillance image captured due to environmental noise, and satellite image due to signal noise and device technical limit.

Figure 6:
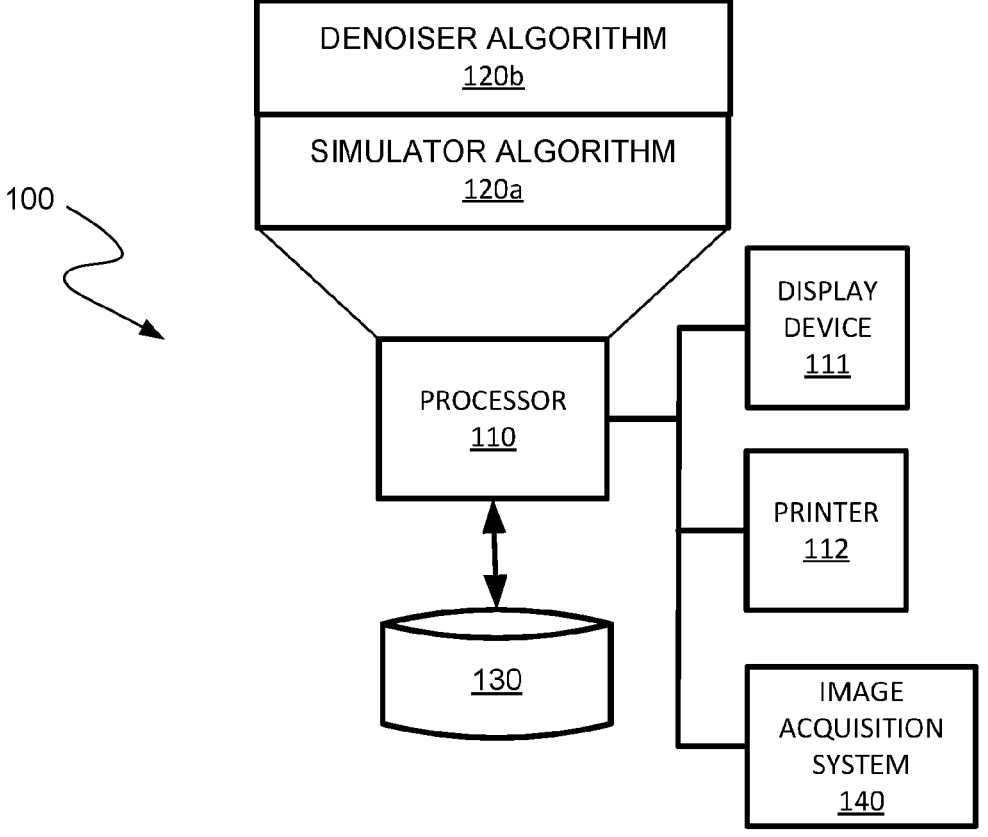
FIG. 6 is a block diagram of an example of an imaging system in accordance with a representative embodiment that is configured to perform the simulator and denoiser algorithms.

FIG. 6 is a block diagram of an example of an imaging system 100 (e.g., a medical imaging system) in accordance with a representative embodiment. A processor 110 of the system 100 is configured to perform the simulator and denoiser algorithms 120a and 120b, respectively, each of which can be implemented in hardware, software, firmware, or a combination thereof. Once trained, the denoiser algorithm 120a can reconstruct high-quality images from noisy image scans (e.g., low-dose CT image scans) captured by a data acquisition system 140 of the imaging system 100, e.g., in the manner described above with reference to FIGS. 1-5. A memory device 130 of the imaging system 100 can be used for storing the computer instructions comprising the programs 120a and 120b and can also comprise a database for storing data used by the denoiser and simulator machine learning models. The imaging system 100 typically includes a display device 150 for displaying information such as, e.g., the reconstructed CT images. The imaging system 100 can comprise a medical imaging system (e.g., CT, MM, PET, etc.) or other appropriate system configured for image acquisition.

CONCLUSIONS

We propose adversarial learning framework using, e.g., a Cyclic Simulation and Denoising (CSD) as an example, for noisy images (e.g., low-dose CT images) restoration. We novelly enable the interaction between noise simulation and denoising in a cyclic training processing. The proposed CSD embraces realistic noise and tissue features into a single unified framework, in which we build a state-of-the-art model for low-dose CT image restoration.

As indicated above, while the examples, experiments and simulations disclosed herein are directed to low-dose CT imaging, the disclosed principles and concepts apply equally to other types of medical imaging technologies, such as, for example, MM imaging and PET imaging (e.g., MM arterial spins, PET, etc.). In addition, the disclosed principles and concepts apply equally to other image acquisitions conditions that introduce noise into the image scan, such as, for example, reduced scan times, lower tracer dose, etc. For example, a wide variety of images with noise, such as natural images captured in dim light, surveillance image captured due to environmental noise, and satellite image due to signal noise and device technical limit can be reconstructed based on the methodology using, e.g., noisy images (e.g., low-dose or exposure images) and images without noise or with reduced noise (e.g., high-dose or exposure images).

It should be noted that any or all portions of algorithms described above that are implemented in software and/or firmware being executed by a processor (e.g., processor 110) can be stored in a non-transitory memory device, such as the memory 130. For any component discussed herein that is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages. The term "executable" means a program file that is in a form that can ultimately be run by the processor 110. Examples of executable programs may be, for example, a compiled program that can be translated into machine code in a format that can be loaded into a random access portion of the memory 130 and run by the processor 110, source code that may be expressed in proper format such as object code that is capable of being loaded into a random access portion of the memory 130 and executed by the processor 110, or source code that may be interpreted by another executable program to generate instructions in a random access portion of the memory 110 to be executed by the processor 110, etc. An executable program may be stored in any portion or component of the memory 130 including, for example, random access memory (RAM), read-only memory (ROM), hard drive, solid-state drive, USB flash drive, memory card, optical disc such as compact disc (CD) or digital versatile disc (DVD), floppy disk, magnetic tape, static random access memory (SRAM), dynamic random access memory (DRAM), magnetic random access memory (MRAM), a programmable read-only memory (PROM), an erasable programmable read-only memory (EPROM), an electrically erasable programmable read-only memory (EEPROM), or other like memory device.

It should be noted that the illustrative embodiments have been described with reference to a few embodiments for the purpose of demonstrating the principles and concepts of the invention. Persons of skill in the art will understand how the principles and concepts of the invention can be applied to other embodiments not explicitly described herein. For example, while particular system arrangements are described herein and shown in the figures, a variety of other system configurations may be used. As will be understood by those skilled in the art in view of the description provided herein, many modifications may be made to the embodiments described herein while still achieving the goals of the invention, and all such modifications are within the scope of the invention.

What is claimed is:

1. An adversarial machine learning and denoising system, comprising:
   a memory device storing a simulator model and a denoiser model; and
   a processor configured to perform the simulator model and the denoiser model, wherein during performance of a simulation-to-denoising (S2D) training cycle of the simulator model and the denoiser model, the simulator model receives as input a low-dose noisy phantom image scan and a high-dose patient image scan and uses the low-dose noisy phantom image scan and the high-dose patient image scan to generate a simulated low-dose noisy patient image scan, and the denoiser model receives the simulated low-dose noisy patient image scan output from the simulator model and uses the simulated low-dose noisy patient image scan to train the denoiser model to remove noise from a real low-dose noisy patient image scan, where low-dose image scans are performed at about 95 mAs or less and high-dose image scans are performed above the low-dose image scans.

2. The adversarial machine learning and denoising system of claim 1, wherein the denoiser model operates as a regularizer for the simulator model during the S2D training cycle by outputting feedback to the simulator model characterizing a noise level of the simulated low-dose noisy patient image scan output by the simulator model, the simulator model using the feedback to train the simulator model to improve the noise level of the simulated low-dose noisy patient image scan.

3. The adversarial machine learning and denoising system of claim 2, wherein during performance of a denoising-to-simulation (D2S) training cycle of the simulator model and the denoiser model, the denoiser model receives as input a low-dose noisy patient image scan and a low-dose noisy phantom image scan and uses the low-dose noisy patient image scan and the low-dose noisy phantom image scan to generate a generated high-dose patient image scan, and the simulator model receives the generated high-dose patient image scan output from the denoiser model and uses the generated high-dose patient image scan and the low-dose noisy phantom image scan to train the simulator model to generate the simulated low-dose noisy patient image scan.

4. The adversarial machine learning and denoising system of claim 3, wherein the simulator model operates as a regularizer for the denoiser model during the D2S training cycle by outputting feedback to the denoiser model that the denoiser model uses to train the denoiser model to improve a noise level of the generated high-dose patient image scan output by the denoiser model.

5. The adversarial machine learning and denoising system of claim 1, wherein phantom image scans are obtained with an anthropomorphic physical phantom model.

6. An adversarial learning and denoising method, comprising:
   during performance of a simulation-to-denoising (S2D) training cycle, receiving as input in a simulator model a low-dose noisy phantom image scan and a high-dose patient image scan and outputting a simulated low-dose noisy patient image scan, where low-dose image scans are performed at about 95 mAs or less and high-dose image scans are performed above the low-dose image scans; and during performance of the S2D training cycle, receiving the simulated low-dose noisy patient image scan output from the simulator model in a denoiser model and using the simulated low-dose noisy patient image scan in the denoiser model to train the denoiser model to remove noise from a real low-dose noisy patient image scan.

7. The adversarial learning and denoising method of claim 6, further comprising:

during the S2D training cycle, operating the denoiser model as a regularizer for the simulator model by outputting feedback to the simulator model characterizing a noise level of the simulated low-dose noisy patient image scan output by the simulator model; and during the S2D training cycle, using the feedback in the simulator model to train the simulator model to improve the noise level of the simulated low-dose noisy patient image scan.

8. The adversarial learning and denoising method of claim 7, further comprising:

during performance of a denoising-to-simulation (D2S) training cycle, receiving as input in the denoiser model a low-dose noisy patient image scan and a low-dose noisy phantom image scan and using the low-dose noisy patient image scan and the low-dose noisy phantom image scan to remove noise from the low-dose noisy patient image scan to generate a generated high-dose patient image scan; and during performance of the D2S training cycle, receiving the generated high-dose patient image scan output from the denoiser model in the simulator model and using the generated high-dose patient image scan to train the simulator model to generate the low-dose noisy patient image scan.

9. The adversarial learning and denoising method of claim 8, further comprising:

during the D2S training cycle, operating the simulator model as a regularizer for the denoiser model by outputting feedback to the denoiser model.

10. The adversarial learning and denoising method of claim 9, further comprising:

during the D2S training cycle, using the feedback output by the simulator model in the denoiser model to train the denoiser model to improve the noise level of the generated high-dose patient image scan generated by the denoiser model.

11. The adversarial learning and denoising method of claim 6, wherein phantom image scans are obtained with an anthropomorphic physical phantom model.

* * * * *